United States Patent [19]

Van Scott et al.

[11] 4,224,339
[45] * Sep. 23, 1980

[54] TREATMENT OF DISTURBED KERATINIZATION

[76] Inventors: Eugene J. Van Scott, 1138 Sewell La., Rydal, Pa. 19046; Ruey J. Yu, 4 Lindenwold Ave., Ambler, Pa. 19002

[*] Notice: The portion of the term of this patent subsequent to Oct. 11, 1994, has been disclaimed.

[21] Appl. No.: 949,536

[22] Filed: Oct. 10, 1978

[51] Int. Cl.$^2$ ................. A61K 31/315; A61K 31/195
[52] U.S. Cl. ..................................... 424/289; 424/70; 424/294; 424/295; 424/316; 424/319; 424/320
[58] Field of Search .............. 424/319, 289, 294, 295, 424/316

[56] References Cited

U.S. PATENT DOCUMENTS 4,053,630  10/1977  Yu et al. .............................. 424/289

OTHER PUBLICATIONS

Stedman's Medical Dictionary, 21st Ed., 1966, pp. 784–785.
Chemical Abstracts 70:68709p (1969).

Primary Examiner—Leonard Schenkman
Attorney, Agent, or Firm—LeBlanc, Nolan, Shur & Nies

[57] ABSTRACT

Preventive as well as therapeutic treatment to alleviate the symptoms of disturbed keratinization, consisting of the topical application of a solution, gel, lotion, cream, ointment, stick, powder or spray containing one or more cysteic acid compounds, is disclosed. The compounds include free acid, ammonium salt, amine salt, metal chelate and metallic salt forms of cysteic acid, cysteine sulfinic acid and homocysteic acid. The efficacious compositions may include the active ingredients present in a total amount of from 0.1 to 30 percent by weight. Topical application to affected areas has been found to achieve from a substantial to a complete remission of dry skin, keratoses, warts and palmar and plantar hyperkeratosis. Used as a hair dressing, the compositions have been found to give the hair excellent grooming and luster.

12 Claims, No Drawings

TREATMENT OF DISTURBED KERATINIZATION

This invention relates to a treatment for disturbed keratinization as well as for hair care to improve grooming and luster. Skin disorders characterized by disturbed keratinization include dry skin, keratoses, warts and palmar and plantar hyperkeratosis.

This invention is related to our prior U.S. patent application Ser. No. 703,188, filed July 7, 1976, now U.S. Pat. No. 4,053,630, issued Oct. 11, 1977. In our aforementioned patent, it was disclosed that cysteic acid, cysteine sulfinic acid and homocysteic acid and chelates thereof were useful in topical application to treat the symptoms of acne, dandruff, and the hereditary skin disorder ichthyosis. These compounds were also found to be effective in treating malodor, and at a symptom alleviating concentration, the compounds exhibited no signs of irritation, burning, or itching of the skin. While the compounds were found to have moderate to complete effectiveness as antiodorants, they had no primary antiperspirant effect.

It has now been discovered, however, that the compositions containing cysteic acid, cysteine sulfinic acid, homocysteic acid or metal chelates thereof, as well as metal salts, ammonium salts and amine salts thereof, have much broader effectiveness against disturbed keratinization conditions, and as a cosmetic hair grooming preparation. Accordingly, the disclosure of our U.S. Pat. No. 4,053,630 is hereby incorporated by reference.

In contrast to the hereditary skin disorder ichthyosis, mild to moderate "dry skin" conditions are quite common. These "dry skin" conditions are specially pronounced during the fall and winter season, when environmental humidity is comparatively low. They are characterized by fissures, cracks or flakes of the skin on hands, face, neck and legs.

Conventional treatments for all kinds of dry skin conditions primarily involve the topical application of oils or oil preparations, and hydrating emollients. In addition, ointments containing salicylic acid, urea, glycerol, propylene glycol, sorbitol or vitamin A have been used. Prior treatments, however, have not been universally successful, and have, in many cases, been unable to promote healing to cause a complete remission of the symptoms. Because the mechanisms involved in causing dry skin are not known, treatment has usually resulted in a temporary remission or healing of the flaky or scaly lesions.

We have now discovered that "dry skin" conditions may be successfully prevented or treated with the free acid, ammonium salt, amine salt, metal chelate and metallic salt forms of cysteic acid, or cysteine sulfinic acid or homocysteic acid, analogues thereof. Generally, the ammonium salt may be formed from the acid and ammonium hydroxide. The amine salt may be formed from an acid and an organic amine. The organic amine may include organic primary, secondary and tertiary amines as well as quarternary ammonium hydroxide compounds.

Preferred organic primary amines include any alkylamines such as methylamine and ethylamine; ethanolamines such as monoethanolamine and monoisopropanolamine; and diamines such as ethylenediamine and 1,2-diaminopropane.

Preferred organic secondary amines include dialkylamines such as dimethylamine and diethylamine; diethanolamine and diisopropanolamine; N-methylethanolamine and N-ethylethanolamine.

Preferred organic tertiary amines may include trialkylamines such as trimethylamine, triethylamine, tripropylamine, N-ethyldicyclohexylamine, tri-iso octylamine, tri-isononylamine and tri-isodecylamine; triethanolamine; N-methyldiethanolamine, N-ethyldiethanolamine, N,N-dimethylethanolamine, N,N-diethylethanolamine and tri-isopropanolamine.

Preferred organic quaternary ammonium hydroxides may include tetra-alkylammonium hydroxide such as tetramethylammonium hydroxide and tetrapropylammonium hydroxide; trialkylethanolammonium hydroxide such as basic choline.

The metal chelate includes a molecular complex of cysteic acid or an analogue thereof and a metal ion such as ferric, cupric, zinc or aluminum ion.

The metallic salt may be formed from an acid and an inorganic alkali such as sodium and potassium hydroxide.

It has been established through tests on humans having "dry skin" conditions that topical application of a lotion, cream or ointment containing from 0.1 to 30 percent of at least one acid, the ammonium salt, the amine salt or metallic salt of the present invention and preferably from 0.2 to 20 percent thereof, is therapeutically effective when applied on a regular basis, to cause, within one to two weeks, a return of the affected areas to a normal skin condition. If two or more acids, ammonium salts, amine salts, metal chelates or metallic salts are used in a composition of the invention, the total concentration of the compounds is preferred not to exceed 20 percent by weight of the composition. It has also been found in humans having frequent occurrence of cracking or flaking skin that topical application of the aforementioned composition of the present invention is effective, when applied on a regular basis, in preventing development of dry skin lesions.

Keratoses of the skin may be classified into two groups, namely actinic and nonactinic keratoses. Actinic keratoses, also known as solar or senile keratoses, are found most commonly in Caucasians with fair colored skin, and almost exclusively in persons with poor ability to tan. Development of actinic keratoses is quite common among people who live in sunny climates such as Australia or the southern United States.

Lesions of actinic keratoses are found only in the sunlight exposed areas of the body such as on the face. The clinical lesion frequently consists of a scaly plaque usually less than 1 cm in diameter with freckled pigmentation varying from yellow, brown to blackish depending on the amount of adherent horny material. In addition, there is usually a pinkish tinge to the entire lesion or a red periphery.

The nonactinic keratoses may be caused by X-ray, radium or chemical carcinogens such as arsenic compounds, or may arise without evident cause. The clinical features of nonactinic keratoses are the same as that of actinic keratoses except that localizations of lesions are not restricted to sunlight exposed areas of the skin.

We have now discovered that actinic and nonactinic keratoses may also be successfully treated with acid, ammonium salt, amine salt, metal chelate or metallic salt forms of cysteic acid, cysteine sulfinic acid or homocysteic acid. When used as a topical agent the therapeutic dose of this cysteic acid or its analogue in solution, gel, lotion, cream, stick, spray or ointment may vary from 0.5 to 20 percent by weight.

Other hyperkeratotic disorders such as warts, and palmar and plantar keratoses may also be successfully treated with acid, ammonium salt, amine salt or metal chelate form of cysteic acid, cysteine sulfinic acid or homocysteic acid. When used as a topical agent, the therapeutic dose of the active ingredient in solution, gel, lotion, cream, stick, powder, spray or ointment may vary from 5 to 30 percent by weight.

It has also been found that the acid, ammonium salt, amine salt, metal chelate and/or metallic salt of cysteic acid, cysteine sulfinic acid or homocysteic acid may be successfully utilized to groom as well as to condition the hair. When used as a topical conditioner for the hair the efficacious dose of the active ingredient in solution, gel, lotion, cream, spray or ointment may vary from 0.2 to 10 percent by weight. The hair thus treated with the instant invention has sheen and luster.

Accordingly, it is the object of this invention to provide a relatively nontoxic, nonallergenic medicinal composition which when topically applied will reliably eradicate or improve the symptoms and signs of dry skin, keratoses, warts, palmar and plantar hyperkeratosis.

It is another object to provide a method for treating disturbed keratinization with a nontoxic solution, gel, lotion, stick, powder, spray, cream or ointment containing cysteic acid, cysteine sulfinic acid or homocysteic acid.

PREPARATION OF THE TERAPEUTIC COMPOSITIONS

In order to prepare the compositions of this invention at least one of cysteic acid, cysteine sulfinic acid and homocysteic acid is first dissolved in water. The solution thus prepared may be admixed with ethanol, propylene glycol or in conventional lotions, creams or ointments.

A typical gel preparation of this invention utilizes at least one of the above compounds, dissolved directly in a mixture of water, ethanol and propylene glycol in a volume ratio of 60:30:10 respectively. A gelling agent such as hydroxyethylcellulose, hydroxypropylcellulose or hydroxypropylmethylcellulose is then added to the mixture with agitation. The preferred concentration of the gelling agent may range from 0.1 to 2 percent by weight of the total composition.

A therapeutic composition of cysteic acid or its analogues may also be prepared in a powder form. Cysteic acid or its analogues may be first ball-milled to a fine powder and then admixed with a talc.

Therapeutic compositions containing cysteic acid or its analogues may also be prepared in a stick form or in a conventionally available spray can, using conventional techniques.

Generally, the concentration of cysteic acid or its analogues ranges from 0.1 to 30% by weight of the total therapeutic composition. The water used to dissolve cysteic acid or its analogues according to this invention may range in concentration from 40 to 90% by weight of the total composition.

To prepare an ammonium salt, an amine salt or a metallic salt of the instant invention cysteic acid, cysteine sulfinic acid or homocysteic acid is allowed to react at room temperature with ammonium hydroxide, an organic amine or an alkali in aqueous solution. Generally, the ammonium salt, amine salt or metallic salt thus formed needs no isolation procedure and may be directly incorporated into the therapeutic composition.

The organic amine may include an organic primary, secondary and tertiary amine as well as a quaternary ammonium hydroxide.

Preferred organic primary amines include any alkylamines such as methylamine and ethylamine, ethanolamines such as monoethanolamine and monoisopropanolamine; and diamines such as ethylenediamine and 1,2-diaminopropane.

Preferred organic secondary amines include dialkylamines such as dimethylamine and diethylamine; diethanolamine and diisopropanolamine; N-methylethanolamine and N-ethylethanolamine.

Preferred organic tertiary amines may include trialkylamines such as trimethylamine, triethylamine, tripropylamine, N-ethyldicyclohexylamine, tri-isooctylamine, tri-isononylamine, and tri-isodecylamine; triethanolamine, N-methyldiethanolamine, N-ethyldiethanolamine, N,N-dimethylethanolamine, N,N-diethylethanolamine and tri-isopropanolamine.

Preferred organic quaternary ammonium hydroxides may include tetraalkylammonium hydroxide such as tetramethylammonium hydroxide and tetrapropylammonium hydroxide; trialkylethanolammonium hydroxide such as basic choline.

Preferred alkalis may include sodium hydroxide and potassium hydroxide.

If a metal chelate of cysteic acid or its analogues is to be used, metallic compounds such as ferric chloride, copper sulfate, copper carbonate, zinc sulfate, zinc oxide, zinc chloride, aluminum chlorhydrate or aluminum zinc sulfate may be added to chelate the cysteic acid or its analogues in solution.

Although on the molecular level one mole of metal ion such as cupric ion may form a copper chelate with one or more than one, mole of cysteic acid or its analogues, it is easier and more practical to prepare the therapeutic composition on a percentage basis, especially when the composition is intended for topical use.

The following are illustrative examples of formulations of compositions according to this invention and it should be understood that the following examples are illustrative and not limited.

EXAMPLE 1

L-Cysteic acid, L-cysteine sulfinic acid or DL-homocysteic acid 2 grams, are dissolved in 50 ml of water. Ethanol, 50 ml was then added to make a 2% concentration.

EXAMPLE 2

L-Cysteic acid, L-cysteine sulfinic acid or DL-homocysteic acid 5 grams was dissolved in 50 ml of water. The solution was admixed with 40 ml of ethanol and 10 ml of propylene glycol to make a 5% composition.

EXAMPLE 3

L-Cysteic acid, L-cysteine sulfinic acid or DL-homocysteic acid 5 grams was dissolved in 10 ml of water and the solution was admixed with 85 grams of hydrophilic ointment, USP until a uniform consistency resulted.

EXAMPLE 4

L-Cysteic acid ($C_3H_7NO_5S \cdot H_2O$) 5,6 g (30 m moles) was dissolved in 70 ml of water and ferric chloride ($FeCl_3 \cdot 6H_2O$), 2.7 g was added to the solution with constant stirring until a clear orange solution formed.

Ethanol, 20 ml and propylene glycol 10 ml were added to the solution to make a composition of cysteic acid chelated with ferric ion.

EXAMPLE 5

L-Cysteic acid ($C_3H_7NO_5S \cdot H_2O$), 1.87 g (10 m mole) was dissolved in 40 ml of water. Cupric sulfate ($CuSO_4 \cdot 5H_2O$), 0.25 g (1 m mole) was then added to the solution with stirring until a clear blue solution formed. Ethanol 50 ml and propylene glycol 10 ml were added to make a composition of copper chelate of cysteic acid.

EXAMPLE 6

L-Cysteic acid, L-cysteine sulfinic acid or DL-homocysteic acid 2 grams was dissolved in 80 ml of water. Cupric carbonate 0.5 gram was added to the solution with stirring until a clear blue solution formed. Ethanol 10 ml and propylene glycol 10 ml were added to the solution to make a composition of copper chelate with cysteic acid or its analogues.

EXAMPLE 7

L-Cysteic acid, L-cysteine sulfinic acid or DL-homocysteic acid 5 grams was dissolved in 50 ml of water. Zinc oxide 1 gram was then added to the solution with stirring until a clear solution formed. Ethanol 40 ml and propylene glycol 10 ml were added to make a composition of zinc chelate with cysteic acid or its analogues.

EXAMPLE 8

L-Cysteic acid, L-cysteinesulfinic acid or DL-homocysteic acid 5 grams was dissolved in 70 ml of water. Zinc chloride 2 grams was then added to the solution with stirring. Ethanol 20 ml and propylene glycol 10 ml were added to make a composition of zinc chelate with cysteic acid or its analogues.

EXAMPLE 9

L-Cysteic acid, L-cysteinesulfinic acid or DL-homocysteic acid 2 grams was dissolved in 70 ml of water. Aluminum chloride ($AlCl_3 \cdot 6H_2O$), 1 gram was added to the solution with stirring. Ethanol 20 ml and propylene glycol 10 ml were added to make a composition of aluminum chelate with cysteic acid or its analogues.

EXAMPLE 10

L-Cysteic acid, L-cysteinesulfinic acid or DL-homocysteic acid 2 grams was dissolved in 40 ml of water. Aluminum zinc sulfate 1 gram was then added to the solution with stirring. Ethanol 50 ml and propylene glycol 10 ml were added to make a composition of aluminum zinc chelate with cysteic acid or its analogues.

EXAMPLE 11

L-Cysteic acid, L-cysteinesulfinic acid or DL-homocysteic acid 10 grams of a fine powder was mixed with 90 grams of fine talc until a uniform powder mixture was obtained. The therapeutic composition of this formulation may be stored in a powder can with holes in the cap at room temperature for extended periods of time without change in therapeutic effectiveness caused by humidity in the air.

EXAMPLE 12

L-Cysteic acid, L-cysteinesulfinic acid or DL-homocysteic acid 2 grams was dissolved in 20 ml of water. N-Methyldiethanolamine 1.2 ml was added to neutralize partially the acidity of the mixture. Ethanol 50 ml and sufficient water were added to make 2% active ingredient in a composition of 50% alcholic aqueous solution.

EXAMPLE 13

Part A:
  Polyoxyethylene sorbitan monooleate: 5 grams
  Cetyl alcohol: 23 grams
  Cholesterol: 0.4 gram
  Squalene: 0.2 gram
Part B:
  Water: 56 ml
  Propylene glycol: 10 ml
  L-Cysteic acid: 5 grams
  Ethanolamine: 1 ml Heat Part A to 70° and heat Part B to 72° C. Add Part B slowly to Part A with agitation. Continue agitation until the mixture is congealed. The water-washable cream thus prepared consists of 5% active ingredient.

EXAMPLE 14

L-Cysteic acid 15 gm is dissolved in 15 ml of hot water, and the solution is admixed with 70 grams of hydrophilic ointment, USP. Continue mixing until a uniform consistency of the cream is obtained. This composition consists of 15% active ingredient in a cream form.

EXAMPLE 15

L-Cysteic acid 20 gm is dissolved in 70 ml of hot water, and 2-pyrrolidinone 10 ml is added to the solution. This composition consists of 20% active ingredient in a solution form.

EXAMPLE 16

L-Cysteic acid 2 gm is dissolved in 70 ml of water and 30 ml of ethanol. Hydroxypropyl cellulose 0.2 gm is then added to the solution with agitation. Continue agitation until a uniform thin gel is obtained.

TEST RESULTS

Dry Skin

Human subjects with mild to moderate degrees of dry skin conditions, as evidenced by dry, cracking or flaking of the skin, were instructed to apply topically the lotion, cream or ointment of the present invention formulated according to Examples 3 or 13 on the affected skin areas. Twice daily topical application was continued for a few weeks. In all 18 human subjects tested, the feeling of skin dryness disappeared after three to four days of topical treatment. In 16 human subjects tested the rough and cracked skin usually became less pronounced within a week. Generally the skin appeared normal and felt smooth after about two weeks of topical treatment.

In contrast to the severe dry skin disease the common dry skin conditions once restored to normal appearing skin remained improved for some time until causes of dry skin, such as low humidity, cold weather, detergents, soaps, chemicals, etc., recurred. On continued use it was also found that twice daily topical application of a composition of the present invention prevented the recurrence of dry skin conditions.

Keratoses

A total of 12 patients having actinic or nonactinic keratoses was selected for this study. Each patient was instructed to apply a test composition, prepared according to Example 14 topically twice daily on the lesions. Standardized color photos were taken of the skin lesions prior to initiating the treatment and after 4 to 8 weeks of topical treatment with the test cream. The test results were determined both by clinical impression and also by comparison of the photos before and after treatment. A total of 7 patients showed substantial reduction in the number of keratotic lesions after four weeks of topical treatment, and complete resolution of most lesions after eight weeks of topical treatment. In the remaining five patients, partial resolution of keratoses had occurred within the eight week interval and required more prolonged topical therapy to cause more complete resolution of lesions.

Warts

Six patients with common warts on the hands and fingers were instructed to apply topically the compositions prepared according to Example 15, three times daily to the lesions. Five patients showed a substantial improvement as evidenced by the reduction in size of the wart lesions after six weeks of topical treatment.

Palmar and Plantar Hyperkeratosis

Seven patients with palmar or plantar hyperkeratosis secondary to chronic inflammatory chronic friction or chronic eczema were instructed to apply topically the compositions prepared according to Example 14 or 15, three times daily to affected areas. All patients showed a substantial improvement after 6 weeks of topical treatment.

Hair Grooming

Seven human subjects were instructed first to shampoo their scalp and hair with any commercially available shampoo product. After shampoo they were advised to apply onto their hair the composition as described in Example 1 or 16. The hair so treated was dried with or without an electric dryer. The hair of all the subjects participating in the study was smooth and lustrous on touch, and in appearance.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed is:

1. A method for treating dry skin, actinic or nonactinic keratoses, warts, and palmar and plantar keratoses skin conditions, said method comprising topically applying to the involved skin a symptom alleviating and therapeutically effective amount of a medicinal composition containing from about 0.1 to 30% by weight of at least one compound selected from the group consisting of cysteic acid, cysteine sulfinic acid and homocysteic acid and chelates of said compound with at least one metallic compound selected from the group consisting of ferric chloride, copper sulfate, copper carbonate, zinc sulfate, zinc oxide, zinc chloride, aluminum chlorohydrate, and aluminum zinc sulfate.

2. The method of claim 1 wherein said compound is present in an amount of from 0.2 to 20% by weight.

3. The method of claim 1 wherein a plurality of said compounds are present in a concentration of no more than about 20% by weight.

4. The method of claim 1 wherein said compound is present in a concentration of from 0.5 to 20% and said method comprises the treatment of actinic and non-actinic keratoses.

5. The method of claim 1 wherein said compound is present in a concentration of from 5 to 30% and said method comprises the method of treatment of warts, palmar, and plantar keratoses.

6. The method of claim 1 wherein said composition further comprises a liquid solution containing water present in from 40 to 90% by weight of the total composition.

7. The method of claim 1 wherein said medicinal composition is in powder form.

8. The method of claim 1 wherein said medicinal composition is a gel.

9. The method of claim 1 wherein said medicinal composition is a water-washable cream.

10. A method for treating dry skin, actinic and non-actinic keratoses, warts, palmar and plantar keratoses, said method comprising topically applying to the involved skin a symptom alleviating and therapeutically effective amount of a medicinal composition containing from about 0.1 to about 30% by weight of at least one compound selected from the group consisting of a reaction product of cysteic acid, cysteine sulfinic acid and homocysteic acid with a base selected from the group consisting of an organic primary, secondary, or tertiary alkylamine, alkanolamine, diamine, dialkylamine, dialkanolamine, alkylalkanolamine, trialkylamine, trialkanolamine, dialkylalkanolamine, or alkydialkanolamine wherein the alkyl or alkanol substituent has from 1 to 10 carbon atoms, an organic quaternary ammonium hydroxide compound, sodium hydroxide, and potassium hydroxide.

11. The method of claim 10 wherein the reaction product comprises a reaction product of a member selected from the group consisting of cysteic acid, cysteine sulfinic acid, homocysteic acid and a base selected from the group consisting of methylamine, ethylamine, ethanolamine, ethylenediamine, 1,2-diaminopropane, dimethylamine, diethylamine, diethanolamine, di-isopropanolamine, N-methylethanolamine, N-ethylethanolamine, trimethylamine, triethylamine, tripropylamine, N-ethyldicyclohexylamine, tri-isooctylamine, tri-isononylamine, tri-isodecylamine, triethanolamine, N-methyldiethanolamine, N-ethyldiethanolamine, N,N-dimethylethanolamine, N,N-diethylethanolamine and tri-isopropanolamine.

12. The method of claim 10 wherein said quaternary ammonium hydroxide compound comprises a member selected from the group consisting of tetramethylammonium hydroxide, tetrapropylammonium hydroxide, and basic choline.

* * * * *